US00PP19926P2

(12) United States Plant Patent
de Jong

(10) Patent No.: US PP19,926 P2
(45) Date of Patent: Apr. 14, 2009

(54) *THUJA* PLANT NAMED 'DE RAKT'

(50) Latin Name: *Thuja plicata*
Varietal Denomination: De Rakt

(76) Inventor: Kees de Jong, Bitswijk 14b, Uden (NL), 5401 JB ( * ) Notice: Subject to any disclaimer, the term of this patent is extended or adjusted under 35 U.S.C. 154(b) by 0 days.

(21) Appl. No.: 12/152,385

(22) Filed: May 14, 2008

(51) Int. Cl.
*A01H 5/00* (2006.01)

(52) U.S. Cl. ..... Plt./213

(58) Field of Classification Search ..... Plt./213
See application file for complete search history.

*Primary Examiner*—Annette H Para
*Assistant Examiner*—Georgia Helmer
(74) *Attorney, Agent, or Firm*—Penny J. Aguirre

(57) ABSTRACT

A new cultivar of *Thuja plicata named* 'De Rakt' characterized by its bright and light green foliage with good color retention throughout the winter, its fine textured foliage, and its narrow columnar growth habit.

2 Drawing Sheets

Botanical classification: *Thuja plicata.*
Varietal denomination: 'De Rakt'.

BACKGROUND OF THE INVENTION

The present invention relates to a new and distinct cultivar of *Thuja plicata* and will be referred to hereafter by its cultivar name, 'De Rakt'. 'De Rakt' represents a new western red cedar, an evergreen tree grown for landscape use.

The inventor discovered this new *Thuja* (un-patented) as a naturally occurring branch mutation of *Thuja plicata* 'Gelderland' (not patented) in May of 1989 in his garden in Uden, The Netherlands by the inventor.

Asexual reproduction of the new cultivar was first accomplished by hardwood cuttings in Uden, the Netherlands in summer of 1999 by the inventor. Further generations of cuttings were taken in following years and trials have determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'De Rakt', as unique from all other selections and forms of *Thuja plicata* known to the inventor.

1. 'De Rakt' exhibits bright light green foliage with good color retention throughout the winter.
2. 'De Rakt' exhibits fine textured foliage.
3. 'De Rakt' exhibits a narrow columnar growth habit.

'De Rakt' differs from its parent plant, 'Gelderland', in having brighter and lighter green foliage that is finer in texture, in having a more narrow plant habit, and in having foliage that retains its foliage color throughout winter; the foliage color of 'Gelderland' that fades to a brown color in winter. 'De Rakt' can be compared to other cultivars of *Thuja plicata* that have a slender form. 'Fastigiata' (not patented) differs in having darker green foliage that turns a muddy brown in winter and 'Atrovirens' (not patented) has shiny green foliage, a broader habit, and also loses its summer foliage color in winter.

BRIEF DESCRIPTION OF THE DRAWING

The plant and plant parts depicted in the accompanied photographs illustrate the unique characteristics of 'De Rakt'. The photographs were taken of a six year-old plant as grown outdoors in a 15-liter container in Uden, The Netherlands.

Figure 1:
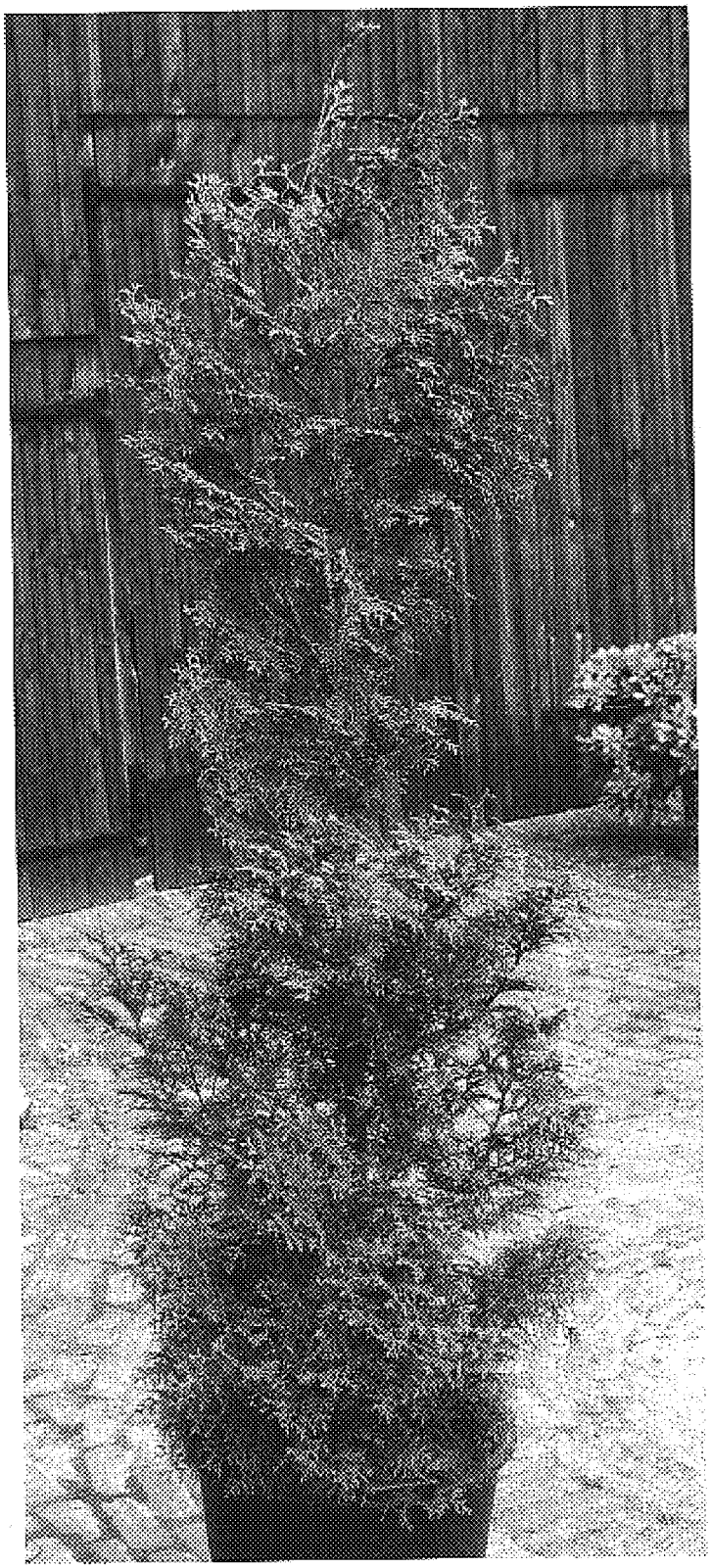
FIG. 1 provides an overall view of the habit and foliage texture of 'De Rakt'.
Figure 2:
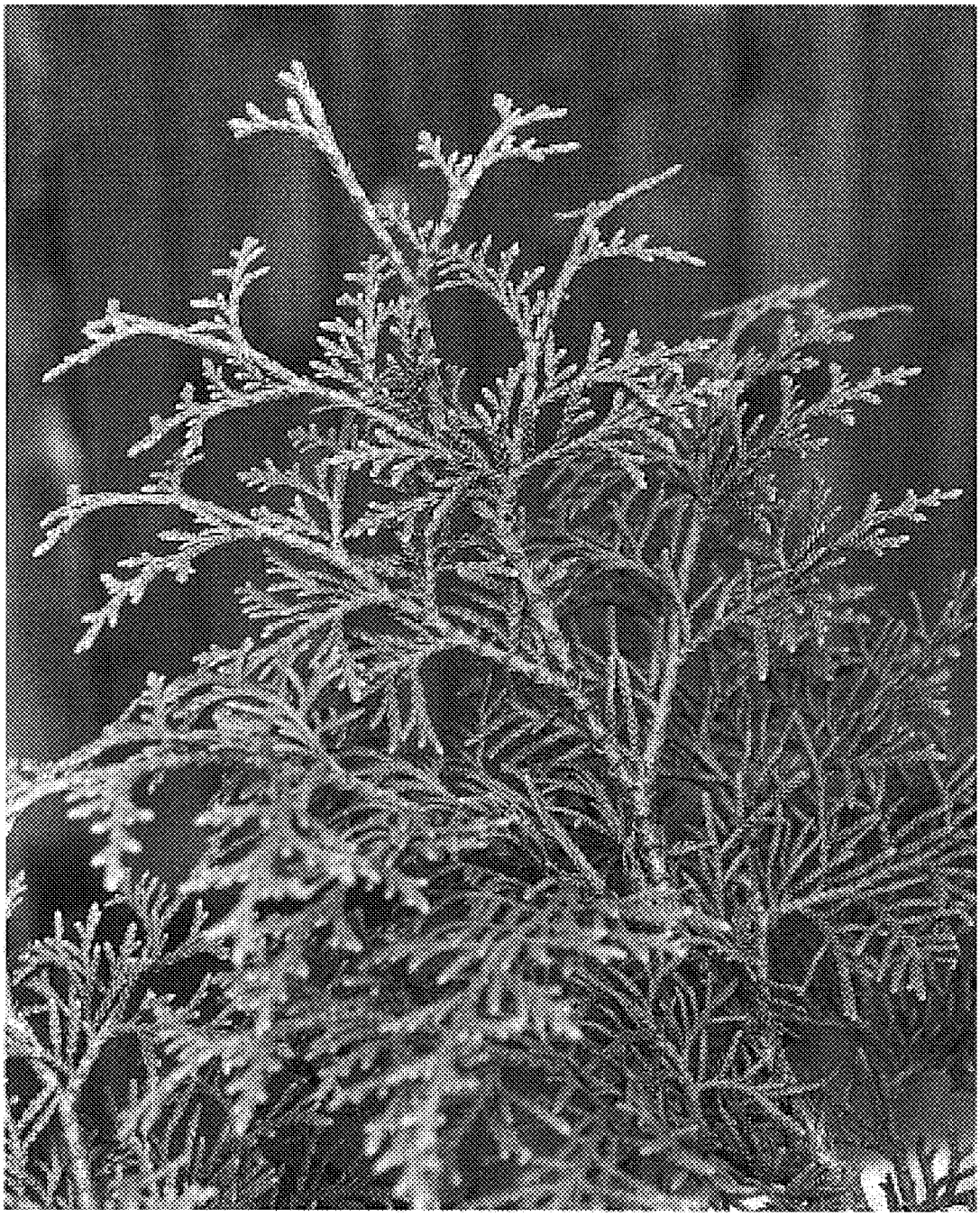
FIG. 2 provides a close-up view of the foliage.

The colors in the photographs are as close as possible with the photographic and printing technology utilized. The color values cited in the detailed botanical description accurately describe the colors of the new *Thuja.*

DETAILED BOTANICAL DESCRIPTION

The following is a detailed description of the new cultivar as taken from six year-old plants as grown in 15-liter containers in Uden, The Netherlands. The plants were grown under average day temperature of 6° to 15° C. and average night temperatures of −2 to 8° C. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General description:

*Plant type.*—Coniferous, evergreen, tree for landscape use.

*Growth habit.*—Narrow columnar with fine foliage.

*Height and spread.*—(6 year-old plants) Average of 181 cm in height and 63 cm in width.

*Cone development.*—Neither male nor female cones have been observed.

*Cold hardiness.*—U.S.D.A. Zone 5.

*Diseases and pests.*—No susceptibility or resistance to diseases or pests known to affect *Thuja* has been observed.

*Root description.*—Fibrous.

*Growth rate.*—Moderate.

Stem description:

*Shape.*—Round to oval.

*Stem size.*—Main branch; average of 1.6 cm in diameter and 180 cm in length, lateral branches; average of 3 mm in diameter and 21.3 cm in length.

*Stem surface.*—Young branches are glabrous and knobby with scales, mature bark is thin, fibrous, fissured into connecting ridges.

*Branching.*—Main stem arises from base with numerous secondary branches, number of lateral branches an average of 55 per main stem 181 cm in length.

*Branch arrangement.*—Alternate (closely on twigs).

*Branch aspect.*—Main stems upright, lateral stems held at about an average of 45° angle from the main stem with sprays that curve upwards.

*Internode length.*—Average of 1.2 cm.

*Stem color.*—New growth on sprays (twigs) are 144C with scales 144A, young branches 165C with scales N167B, branches mature to 200D becoming 200A to 200B with age.

Foliage description:

*Leaf arrangement.*—Numerous leaves arranged on planar branchlets (closely alternate or opposite), scale-like decussate.

*Leaf shape.*—Facial pair keeled, flat pair flattened and oblong.

*Leaf division.*—Simple.

*Leaf base.*—Cuneate.

*Leaf apex.*—Apiculate.

*Leaf venation.*—Not visible.

*Leaf margins.*—Entire.

*Leaf surface.*—Upper and lower; glabrous, smooth, glossy.

*Leaf color.*—Young upper surface; 144A, young lower surface; 144B, mature upper surface; 137A, mature lower surface; 137A to 137B, winter upper surface; 147B, winter lower surface; 138A.

*Leaf fragrance.*—Cedar scented when crushed.

*Leaf size.*—Average of 3.5 mm in length and 15 mm in width.

*Leaf quantity.*—About 1,400 leaves per lateral branch.

Cone description: No cones have been observed on the plants trialed for data collection.

It is claimed:

1. A new and distinct cultivar of *Thuja* plant named 'De Rakt' as herein illustrated and described.

* * * * *